United States Patent
Geisberger et al.

(10) Patent No.: US 7,605,283 B2
(45) Date of Patent: Oct. 20, 2009

(54) PROCESS FOR PREPARING SI-H-CONTAINING SILANES

(75) Inventors: Gilbert Geisberger, Altoetting (DE); Wolfgang Wewers, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/136,981

(22) Filed: Jun. 11, 2008

(65) Prior Publication Data

US 2008/0319214 A1 Dec. 25, 2008

(30) Foreign Application Priority Data

Jun. 20, 2007 (DE) .................. 10 2007 028 254

(51) Int. Cl.
C07F 7/04 (2006.01)

(52) U.S. Cl. .................................. 556/469

(58) Field of Classification Search ............... 556/469
See application file for complete search history.

(56) References Cited

U.S. PATENT DOCUMENTS

| | | | |
|---|---|---|---|
| 3,399,222 A | 8/1968 | Weyenberg | |
| 6,175,029 B1 * | 1/2001 | Colin | 556/469 |
| 2008/0095691 A1 | 4/2008 | Degussa | |

FOREIGN PATENT DOCUMENTS

| | | |
|---|---|---|
| DE | 1264442 B | 3/1968 |
| DE | 3500318 A | 8/1985 |
| DE | 101 57 198 A1 | 5/2002 |
| DE | 10 2004 045 245 A1 | 4/2006 |
| DE | 102004045245 A | 4/2006 |
| EP | 0093640 A | 11/1983 |
| EP | 0 286 074 A2 | 10/1988 |
| EP | 0 685 483 A1 | 12/2006 |
| WO | WO 2006/029930 A1 * | 3/2006 |

OTHER PUBLICATIONS

Belyakova et al., Disproportionation of methyldichloridesilane with Speire's catalyst, (Zhurnal Obshchei Khimii (1989), 59 (3), 724.*
English Abstract corresponding to DE 101 57 198, (2002).
English Abstract corresponding to DE 10 2004 045 245, (2006).
English Abstract corresponding to EP 0 286 074, (1994).
English Abstract corresponding to EP 0 685 483.
Henkel, et al., "Reactor Types and Their Industrial Applications," Ullmann's Encyclopedia of Industrial Chemistry, 7th Edition, v. B4, 2006, pp. 87, 90-93.
Herstellung, A., "Methoden zur Herstellung und Umwandlung von quartaeren Phosphoniumverbindungen, Phosphor-betainen, Phosphin-alkylenen und Pentaorganophosphorverbindungen," Houben-Weyl, Georg Thieme Verlag, v. XII/1, pp. 79-90, 1963.

* cited by examiner

*Primary Examiner*—Jafar Parsa
(74) *Attorney, Agent, or Firm*—Brooks Kushman P.C.

(57) ABSTRACT

Silanes of the general formula (1)

$$R_a SiH_b X_{4-b-a} \qquad (1)$$

are prepared by disproportionating at least one more highly chlorinated silane in the presence of a homogeneous catalyst in an apparatus with at least one reactive distillation column and at least one additional reactor selected from among pre-reactors and side reactors, where R is an alkyl, aryl, alkaryl or haloalkyl radical,
X is a halogen atom,
a is 0 or 1, and
b is 2, 3 or 4.

15 Claims, 3 Drawing Sheets

PROCESS FOR PREPARING SI-H-CONTAINING SILANES

BACKGROUND OF THE INVENTION

1. Field of the Invention

The invention relates to a process for preparing hydrogen-containing silanes by disproportionation of a more highly chlorinated silane in the presence of a homogeneous catalyst.

2. Background Art

The demand for the organylhydrogenchlorosilanes MeSiHCl$_2$ and Me$_2$SiHCl is significantly higher than the amount in which they are obtained as by-products in the direct synthesis by the Müller-Rochow process.

EP 286074 A describes a process for the disproportionation of MeSiHCl$_2$ to give MeSiH$_3$ in the presence of a heterogeneous catalyst in a distillation column. In the process, the heterogeneous catalyst has a limited operating life. To replace the catalyst, it is at least necessary to take the portion of the plant charged with the catalyst out of operation in order for the catalyst to be regenerated in the distillation column. Opening of the distillation column and replacement of the catalyst by fresh catalyst is also frequently necessary.

EP 685483 A describes the disproportionation of MeSiHCl$_2$ to give MeSiH$_3$ in the presence of a homogeneous catalyst in a distillation column. However, the poor space-time yield and the high energy consumption stand in the way of the commercialization of the process.

DE 102004045245 A1 describes the disproportionation of HSiCl$_3$ to prepare SiH$_4$ in the presence of a heterogeneous catalyst in a distillation column provided with at least one side reactor. The heterogeneous catalyst is located in the side reactor and can therefore be replaced more simply.

SUMMARY OF THE INVENTION

It has now been surprisingly discovered that hydrogen-containing silanes may be obtained from more highly chlorinated silanes by disproportionation employing a homogenous catalyst, a reactive distillation column, and at least one prereactor or side reactor. Low energy consumption and high space time yields are achievable by the process.

DETAILED DESCRIPTION OF THE PREFERRED EMBODIMENT(S)

Figure 1:
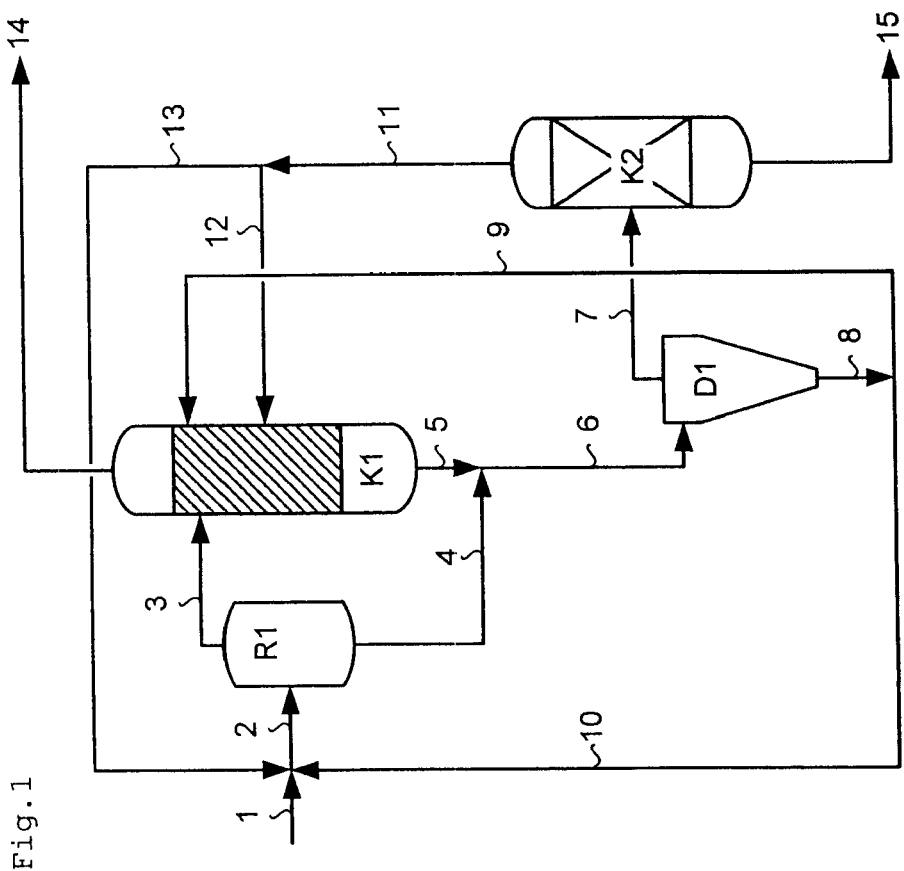
FIG. 1 illustrates one embodiment of a subject invention process in schematic form.

The invention provides a process for preparing silanes of the general formula (1)

$$R_a SiH_b X_{4-b-a} \quad (1)$$

by disproportionation of at least one more highly chlorinated silane in the presence of a homogeneous catalyst in an apparatus which is equipped with at least one reactive distillation column and at least one additional reactor selected from among prereactors and side reactors, where
R is an alkyl, aryl, alkaryl or haloalkyl radical,
X is a halogen atom,
a is 0 or 1 and
b is 2, 3 or 4.

In the present homogeneous process, the combination of prereactor or side reactor with the reactive distillation column and the resulting increased residence time reduces the energy consumption by up to 30% compared to purely a reactive distillation column. Apart from the improved energy consumption, the conversion can be increased at an identical energy input by the combination of reactive distillation column and side reactor/prereactor.

The space-time yields reach values which have been able to be achieved only with heterogeneous catalysts. Here, the homogeneous catalysts bring the advantage that they are pumpable in neat or dissolved form. This makes the process for carrying out the reaction simpler since the catalyst can also be introduced during ongoing operation of the process, i.e. the catalyst concentration can be increased or reduced, the catalyst can be renewed or replaced by another homogeneous catalyst as required.

The additional reactor can be configured as a prereactor or side reactor. Here, the term "prereactor" refers to a reactor in which at least one feed stream is fed into the prereactor and at least one substream is taken from the prereactor and introduced into the reactive distillation column. Direct recirculation of substreams from the reactive distillation column into the prereactor does not take place. The term "side reactor" refers to a reactor in which at least one stream is taken from the reactive distillation column and fed into the side reactor and at least one stream is recirculated from the side reactor into the reactive distillation column. Direct introduction of feed streams into the side reactor does not take place.

Examples of R are alkyl radicals such as the methyl, ethyl, n-propyl, isopropyl, n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radical; hexadecyl radicals and octadecyl radicals such as the n octadecyl radical; cycloalkyl radicals such as cyclopentyl, cyclohexyl, cycloheptyl and methylcyclohexyl radicals; aryl radicals such as the phenyl radical; alkaryl radicals such as the o-, m-, p-tolyl radicals, xylyl radicals, and ethylphenyl radicals; and aralkyl radicals such as the benzyl radical, the α- and ω-phenylethyl radicals; haloalkyl radicals such as the chloromethyl, 3-chloropropyl and 3-bromopropyl radicals; and haloaryl radicals such as the o-, m-, and p-chlorophenyl and chlorotolyl radicals.

The radical R preferably has from 1 to 18 carbon atoms, more preferably from 1 to 6 carbon atoms. In particular, the radical R is a methyl or phenyl radical.

The halogen atom X is preferably chlorine, bromine or iodine.

Preference is given to carrying out the disproportionation reactions (1), (2) and (3) starting from SiHCl$_3$:

$$2SiHCl_3 \rightarrow SiH_2Cl_2 + SiCl_4 \quad (1),$$

$$3SiHCl_3 \rightarrow SiH_3Cl + 2SiCl_4 \quad (2),$$

$$4SiHCl_3 \rightarrow SiH_4 + 3SiCl_4 \quad (3).$$

Particular preference is given to carrying out the disproportionation reactions (4) and (5) starting from MeSiHCl$_2$:

$$2MeSiHCl_2 \rightarrow MeSiH_2Cl + MeSiCl_3 \quad (4),$$

$$3MeSiHCl_2 \rightarrow MeSiH_3 + 2MeSiCl_3 \quad (5).$$

The silanes of the general formula (1) as set forth in claim 1 are preferably used for preparing silanes selected from among MeSiHCl$_2$ and Me$_2$SiHCl.

The homogeneous catalyst preferably contains at least one fully organically substituted ammonium, phosphonium or imidazolium unit. Examples are quaternary ammonium and phosphonium salts and positively charged heterocycles which have one or more fully organically substituted atoms selected from among nitrogen and phosphorus atoms. Preferred positively charged heterocycles are imidazolium salts and pyridinium salts.

As catalysts, preference is given to using:
(a) quaternary ammonium salts of the general formula R$^1_4$NX$^1$ and
(b) quaternary phosphonium salts of the general formula R$^2_4$PX$^2$, where R$^1$ and R$^2$ are each an unsubstituted or halogen-substituted hydrocarbon radical which may contain heteroatoms and X$^1$ and X$^2$ are each a halogen atom.

R$^1$ and R$^2$ can be, for example, branched, unbranched or cyclic alkyl radicals and multiple bond systems such as aryl, alkaryl or aralkyl radicals. Examples of R$^1$ and R$^2$ are the examples of unsubstituted or halogen-substituted alkyl, aryl or alkaryl radicals given above for R and also aralkyl radicals such as o-, m- and p-phenylalkyl radicals. The radicals R$^1$ and R$^2$ preferably have from 1 to 18 carbon atoms, more preferably from 1 to 10 carbon atoms, and the radicals R$^1$ and R$^2$ are each most preferably an alkyl radical having from 2 to 8 carbon atoms.

The halogen atoms X$^1$ and X$^2$ are preferably chlorine, bromine or iodine, in particular chlorine.

The quaternary phosphonium salt is preferably (n-butyl)$_3$(n-octyl)PCl. The preparation of such homogeneous catalysts by alkylation of tertiary phosphines by means of alkyl halides is described, for example, in HOUBEN-WEYL, Georg Thieme Verlag, Volume XII/1, pp. 79-90, 1963.

Further preferred catalysts are:
(c) imidazolium salts of the general formula

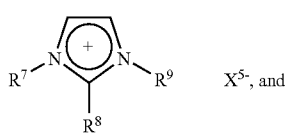

X$^{5-}$, and (d) pyridinium salts of the general formula

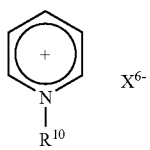

X$^{6-}$ where

R$^8$ is hydrogen and has one of the meanings of R$^1$ and R$^2$, R$^7$, R$^9$ and R$^{10}$ each have one of the meanings of R$^1$ and R$^2$ and X$^5$ and X$^6$ each have one of the meanings of X$^1$ and X$^2$.

Further preferred catalysts are:
(e) ionic liquids, namely low-melting salts of quaternary ammonium, quaternary phosphonium, pyridinium and imidazolium cations. Their preferred melting points at 1 bar are, for the present process, not more than 150° C., preferably not more than 100° C., particularly preferably not more than 50° C.

The radicals of the cations of the ionic liquids preferably correspond to the above-described radicals R$^1$ and R$^2$.

The ionic liquids are preferably used as metal or transition metal halides. The metal and transition metal halides are prepared using, for example, MX$_e$ where M=Ga, Fe, Cu, Zn, In, Ti, Cd, Hg, B, Sn, Pb, Bi and X=halogen. However, it is also possible to use other compositions. They contain, for example, the following anions: AlCl$_4^-$, Al$_2$Cl$_7^-$, Al$_3$Cl$_{10}^-$, AlEtCl$_3^-$, Al$_2$Et$_2$Cl$_5^-$, BCl$_4^-$, BF$_4^-$, Bet$_3$Hex$^-$, CuCl$_2^-$, Cu$_2$Cl$_3^-$, Cu$_3$Cl$_4^-$, SnCl$_3^-$, Sn$_2$Cl$_5^-$, PF$_6^-$, H$_2$PO$_4^-$, SbF$_6^-$, NO$_3^-$, HSO$_4^-$, CH$_3$SO$_4^-$, CF$_3$SO$_3^-$, (CF$_3$SO$_2$)$_2$N$^-$.

Specific examples of ionic liquids are:
1-ethyl-3-methylimidazolium chloride-aluminum chloride (EMIMCL/AlCl$_3$)
1-butyl-3-methylimidazolium chloride-aluminum chloride (BMIMCL/AlCl$_3$)
3-methyl-N-butylpyridinium chloride-aluminum chloride (3-MBPYCL/AlCl$_3$)
1-butylpyridinium chloride-aluminum chloride (BPYCL/AlCl$_3$) tetra-n-butylphosphonium chloride-aluminum chloride (TBPCL/AlCl$_3$).

Particular preference is given to imidazolium salts. Suitable ionic liquids and their preparation are described, for example, in DE 10157198 A.

It is possible to use pure ionic liquids (e) or a mixture of ionic liquids, or mixtures of ionic liquids (e) with salts selected from among the salts (a), (b), (c) and (d). The ionic liquids (e) can also simultaneously function as a solvent or solubilizer for salts selected from among the salts (a), (b), (c) and (d). The ionic liquids are preferably used in a proportion of from 0.1 to 80% by weight, in particular 1-10% by weight, in the reaction mixture with silanes.

The homogeneous catalysts (a), (b), (c) and (d) are soluble in the reaction medium. These catalysts are preferably used neat, as a solution in a preferably high-boiling inert organic solvent, preferably a hydrocarbon such as tetralin or decalin, or as a solution in high-boiling product silanes of the general formula R$_a$SiX$_{4-a}$, where R and X are as defined above.

In the process of the invention, the phosphonium and imidazolium catalysts display excellent thermal stability in the various organylchlorosilane media and a high catalytic activity in the disproportionation reactions according to the invention.

The process of the invention can be carried out batchwise, semicontinuously or fully continuously. It is preferably carried out fully continuously. In the process of the invention, the disproportionation reaction is carried out in an arrangement of reactive distillation and additional reactor. The arrangement according to the invention of the two reactors makes it possible to carry out the disproportionation reaction simply and robustly far beyond the chemical equilibrium. The additional reactor is used to ensure a sufficient residence time. The reactive distillation for its part makes it possible to increase the conversion beyond the chemical equilibrium.

The disproportionation reaction preferably takes place at a pressure of from 0.1 to 20 bar, in particular 1-5 bar, and preferably at a temperature of preferably from 0 to 250° C., in particular from 25 to 150° C.

The silane starting materials are used in gaseous or liquid form or as a solution in an inert organic solvent such as hexane, toluene, xylene or chlorobenzene.

The dichlorosilane and/or monochlorosilane and/or silane prepared in the process of the invention by disproportionation of trichlorosilane is preferably reacted with MeSiCl$_3$ in a subsequent reaction. The target product MeSiHCl$_2$ is obtained in high yields in a comproportionation reaction.

The net equation is then:

$$\text{MeSiCl}_3 + \text{SiHCl}_3 \rightarrow \text{MeSiHCl}_2 + \text{SiCl}_4 \qquad (6).$$

Furthermore, the MeSiH$_2$Cl and/or MeSiH$_3$ prepared in the process of the invention by disproportionation of methyldichlorosilane is preferably reacted with Me$_2$SiCl$_2$ in a subsequent reaction. The target product Me$_2$SiHCl is obtained in high yields in a comproportionation reaction.

The net equation is then:

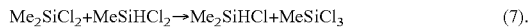

$$\text{Me}_2\text{SiCl}_2 + \text{MeSiHCl}_2 \rightarrow \text{Me}_2\text{SiHCl} + \text{MeSiCl}_3 \qquad (7).$$

The SiH-containing organylchlorosilanes are valuable starting compounds for the preparation of functional silanes or siloxanes which are obtained via a hydrosilylation reaction with organic compounds having aliphatic double or triple bonds. A further use of, for example, dimethylchlorosilane is the preparation of organopolysiloxanes which have dimethylhydrogensilyl groups and are used in addition-crosslinking silicone rubber compositions.

A preferred embodiment of the process of the invention with a prereactor will be explained with the aid of FIG. 1:

Starting materials from streams (1) and (13) and catalyst from stream (10) are mixed and introduced via stream (2) into the prereactor (R1), whereupon disproportionation commences straight away. The conversion in the prereactor (R1) can be increased above the chemical equilibrium by fractional distillation of the reaction products. At the top of the prereactor (R1), the less chlorinated silanes accumulate and are fed as stream (3) to the reactive distillation column (K1). There, they are reacted beyond the chemical equilibrium. The more highly chlorinated silanes containing catalyst leave the prereactor (R1) as bottoms in stream (4). Starting material also enters the reactive distillation column (K1) via stream (12). The reactive distillation column (K1) receives catalyst via stream (9). The less chlorinated silanes are taken off as stream (14) from the top of the reactive distillation column (K1). The more highly chlorinated silanes containing catalyst leave the reactive distillation column (K1) as bottoms in stream (5) and are fed together with stream (4) as stream (6) to the distillation unit (D1) in which they are separated into a silane stream (7) and a catalyst stream (8). The catalyst stream (8) is divided into the streams (9) and (10). The silane stream (7) is fed to a distillation column (K2) from which highly chlorinated silanes are discharged at the bottom as stream (15) and the overhead stream (11) comprising less chlorinated silanes is divided into the streams (12) and (13).

Possible reactor types for the prereactor (R1) are typical liquid-phase reactors as are described, for example, in ULLMANN'S ENCYCLOPEDIA OF INDUSTRIAL CHEMISTRY: 7th edition, 2006. The reactor is particularly preferably configured as a tube reactor, loop reactor or stirred tank reactor or as a reactive distillation.

The reactive distillation column (K1) can, for example, contain ordered packing, random packing elements or trays. Furthermore, the liquid holdup in the reactive distillation column (K1) can be increased by means of suitable internals such as chimney trays or downcomers.

The silanes of the general formula (1) obtained in the disproportionation according to the invention can preferably then be reacted further in a comproportionation reaction. The overall process represents a conversion of chlorosilanes.

The dichlorosilane and/or monochlorosilane and/or silane prepared in the process of the invention by disproportionation of trichlorosilane is preferably reacted with MeSiCl$_3$ in a subsequent reaction. The target product MeSiHCl$_2$ is obtained in high yields in a comproportionation reaction.

Figure 2:
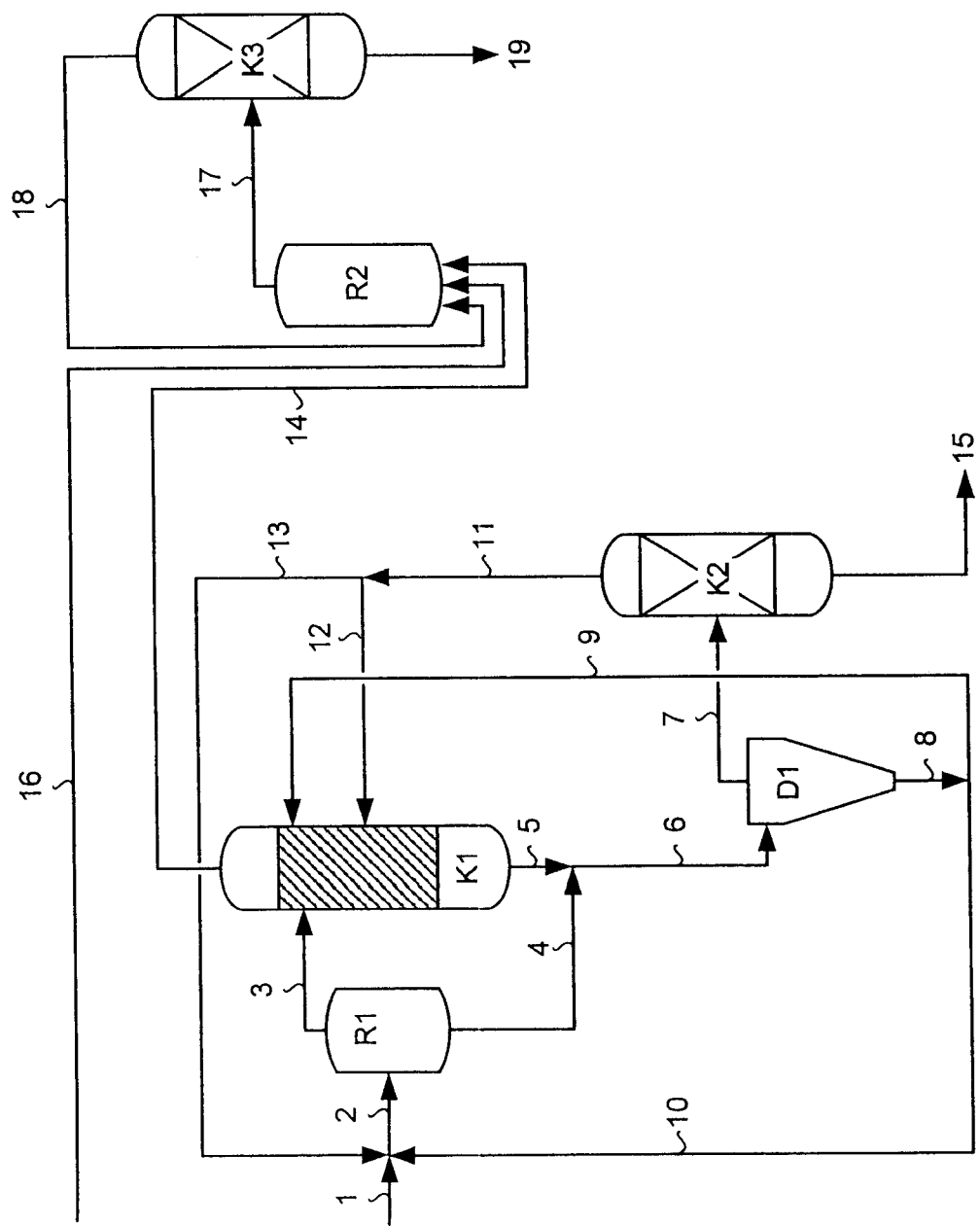
FIG. 2 illustrates a further embodiment of one aspect of the subject invention process.

Such an overall process using a prereactor is explained as a further preferred embodiment of the process of the invention with the aid of FIG. 2: The less chlorinated silanes taken off as stream (14) from the top of the reactive distillation column (K1) are introduced into the comproportionation reactor (R2) together with more highly chlorinated silanes in stream (16) and less chlorinated silanes in stream (18). The silane products in stream (17) from the comproportionation reactor (R2) are separated in the distillation column (K3) into a stream (18) of less chlorinated silanes and a product stream (19) of more highly chlorinated silanes. The less chlorinated silanes in stream (18) are recirculated to the comproportionation reactor (R2).

Figure 3:
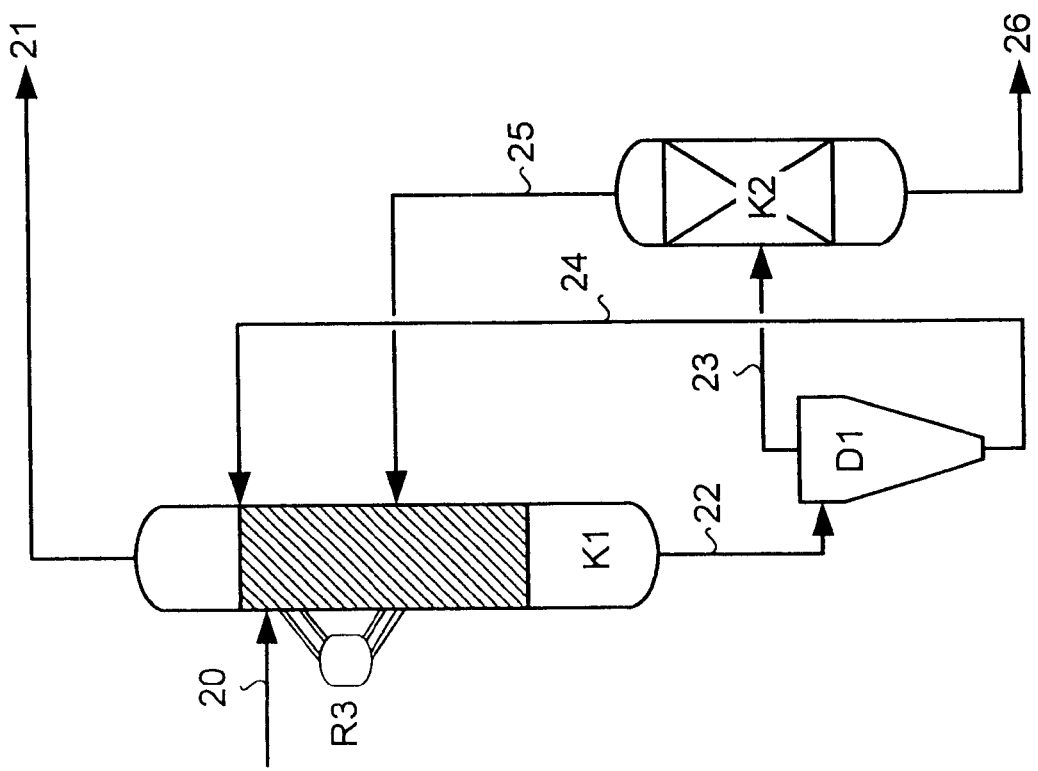
FIG. 3 illustrates one embodiment of the subject invention process employing a side reactor.

A preferred embodiment of the process of the invention with a side reactor is explained with the aid of FIG. 3:

Starting materials are fed as streams (20) and (25) into the reactive distillation column (K1). The catalyst stream (24) is introduced into the reactive distillation column (K1). Part of the reaction mixture in the reactive distillation column (K1) is conveyed through the side reactor (R3). The disproportionation takes place in the reactive distillation column (K1) and in the side reactor (R3). There, the starting materials are reacted beyond the chemical equilibrium. The less chlorinated silanes are taken off as stream (21) from the top of the reactive distillation column (K1). The catalyst-containing more highly chlorinated silanes leave the reactive distillation column (K1) as bottoms in stream (22) and are fed to the distillation unit (D1) in which they are separated into a silane stream (23) and a catalyst stream (24). The catalyst stream (24) is recirculated to the reactive distillation column (K1). The silane stream (23) is fed to the distillation column (K2) from which highly chlorinated silanes are discharged at the bottom as stream (26) and the overhead stream (25) of less chlorinated silanes is recirculated to the reactive distillation column (K1).

An increase in the reaction volume takes place in the side reactor (R3). For this purpose, the liquid phase is collected in the reactive distillation column (K1) and fed into the side reactor (R3). The conversion takes place close to the chemical equilibrium in the side reactor (R3) due to a sufficient residence time. The gas and liquid phases are recirculated from the side reactor (R3) to a suitable point on the reactive distillation column (K1).

All symbols in the above formulae have their respective meanings independently of one another. The silicon atom is tetravalent in all formulae.

In the context of the present invention, all amounts and percentages are, unless indicated otherwise, by weight, all temperatures are 20° C. and all pressures are 1,013 bar (abs.).

EXAMPLES

Example 1

Disproportionation to Prepare Chlorosilanes of the General Formula R$_a$SiH$_b$X$_{4-b-a}$ (1)

a) without Prereactor—not According to the Invention

Figure 4:
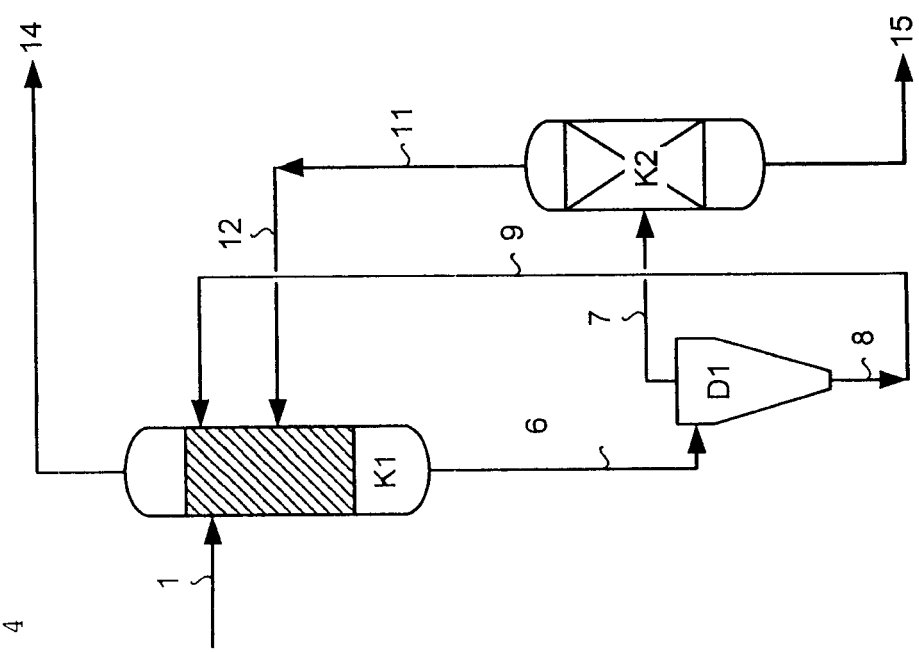
FIG. 4 illustrates a prior art process.

The disproportionation was carried out in an apparatus as shown in FIG. 4. All starting material via stream (1) and all catalyst via stream (8) are fed directly into the reactive distillation column (K1).

b) with Prereactor

The disproportionation was carried out in an apparatus as shown in FIG. 1. When the reaction is carried out in conjunction with the prereactor (R1), the additional reaction volume is provided in the prereactor (R1). The feed mixture of starting material and homogeneous catalyst is introduced into the prereactor (R1).

Carrying out the reaction with prereactor as per example 1b makes it possible, when the prereactor is configured as a tube reactor, to achieve a saving in the heating power required of up to 23% and a saving of 25% in the cooling power (see Table 1). Apart from the lower energy consumption, example 1b) gives a space-time yield which is up to 17% higher than in example 1a), which leads to smaller reactor dimensions.

Table 1:

Relative energy consumption and space-time yield as a function of the installed volume of the prereactor at a constant total conversion of the process. The first line shows the ratio of the prereactor (R1) to the reaction volume in the reactive distillation (K1). At a ratio of 0, a pure reactive distillation as per Example 1a is present for comparative purposes.

| Volume of prereactor/volume of reactive distillation | [—] | 0.000 | 0.048 | 0.096 | 0.243 | 0.488 |
|---|---|---|---|---|---|---|
| Relative heating power | [%] | 100.0% | 94.5% | 91.3% | 85.3% | 81.4% |
| Relative cooling power | [%] | 100.0% | 94.1% | 90.9% | 84.6% | 80.4% |
| Relative space-time yield | [%] | 100.0% | 104.6% | 107.9% | 113.8% | 116.5% |

TABLE 2

Main constituents of the streams from Example 1 for the disproportionation of $SiHCl_3$ and $MeSiHCl_2$

| Stream | $SiHCl_3$ disproportionation | $MeSiHCl_2$ disproportionation |
|---|---|---|
| 1 | $SiHCl_3$ | $MeSiHCl_2$ |
| 2 | $SiHCl_3$; catalyst | $MeSiHCl_2$ |
| 3 | $SiH_3Cl$; $SiH_2Cl_2$; $SiHCl_3$ | $MeSiH_2Cl$; $MeSiHCl_2$ |
| 4 | $SiHCl_3$; $SiCl_4$; catalyst | $MeSiHCl_2$; $MeSiCl_3$; catalyst |
| 5 | $SiHCl_3$; $SiCl_4$; catalyst | $MeSiHCl_2$; $MeSiCl_3$; catalyst |
| 6 | $SiHCl_3$; $SiCl_4$; catalyst | $MeSiHCl_2$; $MeSiCl_3$; catalyst |
| 7 | $SiHCl_3$; $SiCl_4$ | $MeSiHCl_2$; $MeSiCl_3$ |
| 8 | Catalyst | Catalyst |
| 9 | Catalyst | Catalyst |
| 10 | Catalyst | Catalyst |
| 11 | $SiHCl_3$ | $MeSiHCl_2$ |
| 12 | $SiHCl_3$ | $MeSiHCl_2$ |
| 13 | $SiHCl_3$ | $MeSiHCl_2$ |
| 14 | $SiH_4$; $SiH_3Cl$; $SiH_2Cl_2$ | $MeSiH_3$ |
| 15 | $SiCl_4$ | $MeSiCl_3$ |

Example 2

Disproportionation to Prepare Chlorosilanes of the General Formula $R_aSiH_bX_{4-b-a}$ (1) with Side Reactor The disproportionation was carried out in an apparatus as shown in FIG. 3.

TABLE 3

Main constituents of the streams from Example 2 for the disproportionation of SiHCl3 and MeSiHCl2

| Stream | $SiHCl_3$, disproportionation | $MeSiHCl_2$ disproportionation |
|---|---|---|
| 20 | $SiHCl_3$ | $MeSiHCl_2$ |
| 21 | $SiH_4$; $SiH_3Cl$; $SiH_2Cl_2$ | $MeSiH_3$ |

TABLE 3-continued

Main constituents of the streams from Example 2 for the disproportionation of SiHCl3 and MeSiHCl2

| Stream | $SiHCl_3$, disproportionation | $MeSiHCl_2$ disproportionation |
|---|---|---|
| 22 | $SiHCl_3$; $SiCl_4$; catalyst | $MeSiHCl_2$; $MeSiCl_3$; catalyst |
| 23 | $SiHCl_3$; $SiCl_4$ | $MeSiHCl_2$; $MeSiCl_3$ |
| 24 | Catalyst | Catalyst |
| 25 | $SiHCl_3$ | $MeSiHCl_2$ |
| 26 | $SiCl_4$ | $MeSiCl_3$ |

Example 3

Process for the Conversion of Chlorosilanes of the General Formula $R_aSiH_bX_{4-b-a}$ (1) using a Prereactor The disproportionation was carried out in an apparatus as shown in FIG. 2.

TABLE 4

Main constituents and mass flows of the streams from Example 3

| Stream | $SiHCl_3$ disproportionation | $MeSiHCl_2$ disproportionation Constituents | Mass flow kg/h |
|---|---|---|---|
| 1 | $SiHCl_3$ | $MeSiHCl_2$ | 10.0 |
| 2 | $SiHCl_3$; catalyst | $MeSiHCl_2$ | 11.4 |
| 3 | $SiH_3Cl$; $SiH_2Cl_2$; $SiHCl_3$ | $MeSiH_2Cl$; $MeSiHCl_2$ | 2.4 |
| 4 | $SiHCl_3$; $SiCl_4$; catalyst | $MeSiHCl_2$; $MeSiCl_3$; catalyst | 9.0 |
| 5 | $SiHCl_3$; $SiCl_4$; catalyst | $MeSiHCl_2$; $MeSiCl_3$; catalyst | 17.5 |
| 6 | $SiHCl_3$; $SiCl_4$; catalyst | $MeSiHCl_2$; $MeSiCl_3$; catalyst | 26.4 |
| 7 | $SiHCl_3$; $SiCl_4$ | $MeSiHCl_2$; $MeSiCl_3$ | 23.0 |
| 8 | Catalyst | Catalyst | 3.4 |
| 9 | Catalyst | Catalyst | 2.1 |
| 10 | Catalyst | Catalyst | 1.4 |
| 11 | $SiHCl_3$ | $MeSiHCl_2$ | 14.7 |
| 12 | $SiHCl_3$ | $MeSiHCl_2$ | 14.7 |
| 13 | $SiHCl_3$ | $MeSiHCl_2$ | 0.0 |
| 14 | $SiH_4$; $SiH_3Cl$; $SiH_2Cl_2$ | $MeSiH_3$; $MeSiH_2Cl$ | 1.7 |
| 15 | $SiCl_4$ | $MeSiCl_3$ | 8.3 |
| 16 | $MeSiCl_3$ | $Me_2SiCl_2$ | 18.1 |
| 17 | $SiH_4$; $SiH_3Cl$; $SiH_2Cl_2$; $SiHCl_3$; $MeSiHCl_2$; $MeSiCl_3$ | $MeSiH_3$; $MeSiH_2Cl$; $MeSiHCl_2$; $Me_2SiHCl$; $Me_2SiCl_2$ | 30.1 |
| 18 | $SiH_4$; $SiH_3Cl$; $SiH_2Cl_2$ | $MeSiH_3$; $MeSiH_2Cl$ | 10.4 |
| 19 | $SiHCl_3$; $MeSiHCl_2$; $MeSiCl_3$ | $MeSiHCl_2$; $Me_2SiHCl$; $Me_2SiCl_2$ | 19.7 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing silanes of the formula (1)

$$R_aSiH_bX_{4-b-a} \qquad (1)$$

comprising disproportionating at least one more highly chlorinated silane in the presence of a homogeneous catalyst in an apparatus which is equipped with at least one reactive distillation column and at least one additional prereactor and/or side reactor, where R is an alkyl, aryl, alkaryl or haloalkyl radical,
X is a halogen atom,
a is 0 or 1 and
b is 2, 3 or 4.

2. The process of claim 1, wherein the radical R is a methyl or phenyl radical and the halogen atom X is chlorine.

3. The process of claim 1, wherein at least one of disproportionation reaction (1), (2) and (3) starting from SiHCl$_3$ are carried out:

$$2SiHCl_3 \rightarrow SiH_2Cl_2 + SiCl_4 \quad (1),$$

$$3SiHCl_3 \rightarrow SiH_3Cl + 2SiCl_4 \quad (2),$$

$$4SiHCl_3 \rightarrow SiH_4 + 3SiCl_4 \quad (3).$$

4. The process of any of claim 1, wherein at least one of disproportionation reaction (4) and (5) starting from MeSiHCl$_2$ are carried out:

$$2MeSiHCl_2 \rightarrow MeSiH_2Cl + MeSiCl_3 \quad (4),$$

$$3MeSiHCl_2 \rightarrow MeSiH_3 + 2MeSiCl_3 \quad (5).$$

5. The process of claim 1, wherein the silanes of the formula (1) are used for preparing silanes MeSiHCl$_2$ and Me$_2$SiHCl.

6. The process of claim 1, wherein the homogeneous catalyst comprises at least one fully organically substituted ammonium, phosphonium or imidazolium moiety.

7. The process of claim 1, which employs a prereactor, there being no direct recycle of a substream from the reactive distillation column into the prereactor.

8. The process of claim 1, wherein a prereactor and a side reactor are employed.

9. The process of claim 1, wherein the homogenous catalyst comprises a catalyst dissolved in an ionic liquid.

10. The process of claim 1, wherein the homogenous catalyst is an ionic liquid.

11. The process of claim 10, wherein said ionic liquid comprises a salt of a quaternary ammonium, quaternary phosphonium, pyridinium, or imidazolium cation, or mixture thereof, the ionic liquid having a melting point of not more than 150° C.

12. The process of claim 1, wherein the catalyst comprises at least one of:
1-ethyl-3-methylimidazolium chloride-aluminum chloride;
1-butyl-3-methylimidazolium chloride-aluminum chloride;
3-methyl-N-butylpyridinium chloride-aluminum chloride;
1-butylpyridinium chloride-aluminum chloride; and
tetra-n-butylphosphonium chloride-aluminum chloride.

13. The process of claim 1, wherein the catalyst is supplied as a solution in a high boiling inert organic solvent.

14. The process of claim 13, wherein the high boiling inert solvent comprises at least one of tetralin or decalin.

15. The process of claim 1, further comprising removing a stream of less chlorinated silanes from the top of the reactive distillation column and introducing the less chlorinated silanes into a comproportionation reactor, feeding a product stream from the comproportionation reactor into a distillation column, and separating the product stream into respective further product streams of less chlorinated silanes and more chlorinated silanes.

* * * * *